(12) United States Patent
Simkin et al.

(10) Patent No.: US 7,264,629 B2
(45) Date of Patent: Sep. 4, 2007

(54) PHOTODYNAMIC THERAPY FOR THE TREATMENT OF HAIR LOSS

(75) Inventors: Guillermo O. Simkin, North Vancouver (CA); Anna M. Richter, Vancouver (CA); David W. C. Hunt, Surrey (CA); John Robert North, Vancouver (CA); Peter Lutwyche, Vancouver (CA); Ronald Erwin Boch, Vancouver (CA); Jean-Marie Houle, Vancouver (CA)

(73) Assignee: QLT, Inc., Vancouver (CA)

( * ) Notice: Subject to any disclaimer, the term of this patent is extended or adjusted under 35 U.S.C. 154(b) by 599 days.

(21) Appl. No.: 10/422,363

(22) Filed: Apr. 23, 2003

(65) Prior Publication Data

US 2004/0029856 A1 Feb. 12, 2004

Related U.S. Application Data

(63) Continuation-in-part of application No. 10/291,795, filed on Nov. 8, 2002, now Pat. No. 7,090,691.

(60) Provisional application No. 60/338,295, filed on Nov. 9, 2001.

(51) Int. Cl.
*A61N 5/06* (2006.01)
*A61B 18/18* (2006.01)

(52) U.S. Cl. .............................. 607/88; 607/89; 606/9; 128/898

(58) Field of Classification Search ............ 607/88–91, 607/94; 606/3, 9; 128/898
See application file for complete search history.

(56) References Cited

U.S. PATENT DOCUMENTS

| | | | |
|---|---|---|---|
| 4,753,958 A | 6/1988 | Weinstein et al. | 514/410 |
| 5,171,749 A | 12/1992 | Levy et al. | |
| 5,283,255 A | 2/1994 | Levy et al. | 514/410 |
| 5,669,916 A | 9/1997 | Anderson | 606/133 |
| 5,824,643 A | 10/1998 | Pierce et al. | |
| 5,830,177 A * | 11/1998 | Li et al. | 604/22 |
| 5,871,480 A | 2/1999 | Tankovich | 606/9 |
| 5,989,267 A | 11/1999 | Anderson | 606/133 |

(Continued)

FOREIGN PATENT DOCUMENTS

EP 0 350 036 1/1990

(Continued)

OTHER PUBLICATIONS

Chiu, H. et al., "Human Hair Follicle Dermal Papilla Cell, Dermal Sheath Cell and Interstitial Dermal Fibroblast Characteristics" J Formos NMed Assoc 95(9):667-74 (1996).

(Continued)

*Primary Examiner*—A. Farah
(74) *Attorney, Agent, or Firm*—Morrison & Foerster LLP (57) ABSTRACT

Photodynamic therapy (PDT) is used to stimulate and/or restore hair growth in areas of hair loss. Methods and compositions relating to PDT treatment for alopecia are disclosed. In light of PDT use to remove unwanted hair by inactivating or destroying hair follicles or destroying the tissue feeding the hair follicles, such methods and compositions relate to a surprising and unexpected discovery. PDT permits a means to treat conditions relating to hair loss such as androgenic alopecia, alopecia areata and drug-induced alopecia.

47 Claims, 3 Drawing Sheets

U.S. PATENT DOCUMENTS

| | | | |
|---|---|---|---|
| 6,050,990 A | 4/2000 | Tankovich et al. | 606/9 |
| 6,294,192 B1 | 9/2001 | Patel et al. | 424/451 |
| 6,607,522 B1 | 8/2003 | Hamblin et al. | |
| 6,629,971 B2 | 10/2003 | McDaniel | 606/9 |
| 6,676,655 B2 | 1/2004 | McDaniel | |
| 6,849,584 B2 | 2/2005 | Geary et al. | |
| 6,916,316 B2* | 7/2005 | Jay | 606/9 |
| 6,936,044 B2* | 8/2005 | McDaniel | 606/9 |
| 7,015,209 B2* | 3/2006 | Takahashi et al. | 514/120 |
| 7,090,691 B2* | 8/2006 | Simkin et al. | 607/88 |
| 2003/0170822 A1 | 9/2003 | Itoh | |
| 2003/0199403 A1 | 10/2003 | Wells et al. | |
| 2004/0033493 A1 | 2/2004 | Tchernev et al. | |
| 2006/0265028 A1* | 11/2006 | Houle et al. | 607/88 |

FOREIGN PATENT DOCUMENTS

| | | |
|---|---|---|
| EP | 1 138 349 | 10/2001 |
| EP | 1 147 785 | 10/2001 |
| FR | 2 693 906 | 1/1994 |
| WO | WO88/05653 | 8/1988 |
| WO | WO95/07077 | 3/1995 |
| WO | WO97/32046 | 9/1997 |
| WO | WO98/50387 | 11/1998 |
| WO | WO99/59556 | 11/1999 |
| WO | WO-00/32121 | 6/2000 |
| WO | WO 00/59475 | 10/2000 |
| WO | WO 00/64476 | 11/2000 |
| WO | WO 01/08660 | 2/2001 |
| WO | WO 01/85212 | 11/2001 |
| WO | WO 01/85213 | 11/2001 |

OTHER PUBLICATIONS

De Villez et al., Journal of the American Academy of Dermatology 16(3 Part 2):669-672 (1987).

De Vree, W. et al., "Role of Interleukin I and Granulocyte Colony-Stimulating Factor in Photofrin-Based Photodynamic Therapy of Rat Rhabdomyosarcoma Tumors" Cancer Res. 57(13):2555-8 (1997).

Kick, G. et al., "Strong and Prolonged Induction of C-Jun and C-Fos Proto-Oncogenes by Photodynamic Therapy" Br J Cancer 74(1):30-6 (1996).

* cited by examiner

PHOTODYNAMIC THERAPY FOR THE TREATMENT OF HAIR LOSS

RELATED APPLICATIONS

This application is a continuation-in-part of U.S. patent application Ser. 10/291,795, filed Nov. 8, 2002 now U.S. Pat. No. 7,090,691, which claims priority to U.S. Provisional Application 60/338,295, filed Nov. 9, 2001, which are both hereby incorporated in their entireties as if fully set forth.

FIELD OF THE INVENTION

This invention relates to the use of photodynamic therapy (PDT) and the use of PDT with appropriate photosensitizers to stimulate hair growth. In particular, the use of photosensitizers and PDT for treating conditions relating to hair loss, such as androgenetic alopecia and alopecia areata, is described. The present invention further relates to increases in proinflammatory cytokines induced by PDT, which stimulates hair growth, as well as to methods of determining the level of hair growth stimulation mediated by PDT.

BACKGROUND OF THE INVENTION

Alopecia is the general term referring to any disease or condition involving hair loss. There are several different types of hair loss, the most common being androgenetic alopecia (AGA; see Sawaya, M. E. *Seminars in Cutaneous Medicine and Surgery* 17(4):276-283, 1998), alopecia areata (AA; see Fiedler & Alaiti, *Dermatologic Clinics* 14(4): 733-738, 1996, as well as chemotherapy and drug-induced alopecia.

Androgenetic alopecia (AGA) is by far the most common type of alopecia. AGA is a patterned, progressive loss of an excessive amount of hair from the scalp. Significant AGA occurs in 50% of men by the age of fifty and 50% of women by the age of sixty. AGA is believed to be a result of both genetic predisposition and the presence of a sufficient level of circulating androgens. It is thought that the enzyme 5 alpha reductase present in dermal papilla cells converts testosterone to dihydrotestosterone (DHT). DHT binds to androgen receptors, also localized in the dermal papilla cells, triggering changes in the hair follicle that result in (1) shortening of the anagen or growth phase of the hair cycle, (2) development of a latent phase in the hair cycle following shedding of the telogen hair, and (3) follicular miniaturization process that reduces the caliber of the anagen hairs produced. It is thought that differential expression of 5-alpha reductase and/or androgen receptors in various types of hair follicles accounts for patterned hair growth and loss.

Currently approved treatments for AGA include minoxidil (Rogaine™), an anti-hypertensive drug for which the mechanism of action in promoting hair growth is unknown. Minoxidil must be applied topically on a twice daily basis, and is therefore somewhat inconvenient to use. Studies have shown that 2% Minoxidil can provide an increase in the numbers of terminal hairs after 4-12 months (De Villez et al, *Journal of the American Academy of Dermatology*, Vol. 16, No. 3, Part 2 (Mar. 1987) 669-672). However, this benefit disappears over time or once the treatment is stopped. Another drug used in the treatment of AGA is finasteride (Propecia™), a selective inhibitor of the type 2 isoenzyme 5-alpha reductase. This treatment has marginal efficacy, requires daily oral administration and can have some anti-androgenic side effects such as alteration of libido. Hair transplants and scalp reduction are also performed on patients with hair loss associated with AGA. These procedures are too expensive or time consuming for many people. In addition, many people are put off by the surgical nature of the treatment.

Alopecia areata (AA) has been reported to account for 2% of new outpatients in dermatology clinics (Fiedler & Alaiti supra). AA is a nonscarring form of hair loss which occurs in humans and other species and is thought to be due to an inflammatory reaction caused by autoimmune response directed against the anagen stage hair follicle structure (McElwee et al. *Pathobiology* 66(2): 90-107, 1998).

A number of therapeutic modalities have been tested for the treatment of AA, with variable results ranging from no effect to partial or full hair regrowth. In some cases chronic maintenance treatment is required. Major drawbacks of these treatments are side effects, which can be local or systemic in nature. Fiedler & Alaiti (supra) and Shapiro (*Dermatological Clinics* 11(1): 35-46, 1993) have reviewed the various treatments available for AA, including steroids (topical, intralesional and systemic), minoxidil, anthralin, photochemotherapy, cyclosporin A and other agents, as well as combination treatments.

Photochemotherapy therapy for AA using psoralen and high energy UVA (PUVA) treatment has met with very limited success and its effectiveness for AA is in doubt (Lebwohl, M. Lancet 349:222-223, 1997). Side effects of PUVA treatment such as nausea, pigmentary changes, risk of skin cancer formation, and cataracts have been reported (Fiedler & Alaiti, supra). Antioxidants have been used to ameliorate the side-effects of PUVA therapy (Ptapenko & Kyagova, *Membr. Cell Biol.* 12(2): 269-278, 1998). The use of 2% khellin, a compound with a chemical structure that resembles psoralen, and UVA for alopecia areata was found to be successful in 5 of the 10 patients tested (Orasa et al. *Int. J. Dermatol.* 32(9): 690, 1993). Since khellin did not cause phototoxicity, the authors have suggested its use as an alternative to psoralen.

Hematoporphyrin and high energy UVA has been used in a very limited study by Monfrcola et al. (*Photodermatology* 4:305-306, 1987). Two patients were treated with topical hematoporphyrin (0.5%, HP) and UVA irradiation with three times a week for eight weeks. In the first week of treatment there was significant erythema and mild scaling followed by hyperpigmentation in the HP treated sites. Side effects included unpleasant reddish skin coloration for several hours and sometimes burning sensations during the irradiation phase. The authors point out that severe phototoxic reactions could occur with the use of HP concentrations greater than 1%. They also state that more work is needed before this approach can be subject to routine clinical use.

Photodynamic therapy (PDT) has been utilized for the removal of unwanted hair in human subjects. Briefly the treatment involves a topical application of a photosensitizer on a selected area of the skin, a period for absorption of the photosensitizer, followed by a pulse or continuous irradiation or vibration of the area. The process involves inactivating or destroying the hair follicles or destroying the tissue feeding the hair follicles (see U.S. Pat. Nos. 5,669,916; 5,871,480; WO 97/32046).

Photodynamic therapy is a minimally invasive two-step medical procedure that uses photoactivatable drugs called photosensitizers to treat a range of diseases. First, a photosensitizer is administered and, once it has permeated the target tissue, the photosensitizer is then activated by exposure to a dose of electromagnetic (usually light) radiation at a particular wavelength. Photodynamic therapies have been approved for a number of indications including the treatment of non-small cell lung cancer (Photofrin™), age-related macular degeneration (Visudyne™), actinic keratosis (Metvix™, Levulan™), and basal cell carcinoma (Metvix™).

There continues to be a need for an effective, non-surgical procedure that results in a rapid increase in the number of terminal hairs but has minimal side effects.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It has been discovered that photodynamic therapy (PDT) can stimulate hair growth and restore hair growth in areas of hair loss. The discovery includes the ability to use a variety of photosensitizers in PDT to treat hair growth reduction or hair loss. In light of the use of PDT to remove unwanted hair by inactivating or destroying hair follicles or destroying the tissue feeding the hair follicles, as discussed above, the instant invention relates to a surprising and unexpected discovery.

The instant invention provides methods and compositions for treating lack of hair growth or a reduction or loss of existing hair by stimulating and/or restoring hair growth with PDT. Thus one aspect of the invention relates to methods for stimulating, inducing, restoring, reviving, renewing, replacing or otherwise activating hair growth in animals characterized by a lack of hair growth or a reduction in the amount of, or loss of, hair. In particular, the treatment methods of the invention comprise i) administering an effective and/or sufficient amount of photosensitizer resulting in an effective or desired degree of biodistribution; ii) irradiating at least a portion of the external surface of the animal with light including one or more wavelengths capable of activating said photosensitizer for a time period sufficient to activate the photosensitizer. The administrating and irradiating acts of (i) and (ii) may be repeated as necessary or desired to result in a desired level of hair growth.

The desired therapeutic response of hair growth can also be accomplished by the irradiation of skin, which has been treated with an effective amount of a photosensitizer, with light including one or more wavelengths capable of activating said photosensitizer for a time period sufficient to activate the photosensitizer and result in a desired level of hair growth. Moreover, the methods of the invention may be practiced with any photosensitizer, which may be delivered systemically or locally.

Thus in one application of the invention, the invention provide for the use of photodynamic therapy (PDT) to stimulate an increase in hair count numbers and restore hair growth in areas of hair loss. One embodiment of this application comprises:
  (a) administering an effective and/or sufficient amount of a photosensitizer to an area of a subject's skin where hair growth is desired; and
  (b) irradiating the area with electromagnetic energy containing a wavelength capable of activating, or appropriate to activate, said photosensitizer for a time period sufficient to activate the photosensitizer; and optionally
  (c) repeating (a) and (b)

wherein there is an increase in hair count numbers in the treated area.

Preferably, the increase in hair count is an increase in terminal hairs, which are long, pigmented hairs that are produced by follicles with sebaceous (oil) glands. They are found on the scalp, beard, armpits and pubic areas and are in contrast to vellus hairs, which are short hairs, often only a centimeter or two long, that contain little or no pigment. The follicles that produce vellus hairs do not have sebaceous and never produce any other kind of hairs. Terminal hairs also differ from Lanugo hair, which develops on an unborn baby. In people who have inherited a tendency to baldness terminal hairs may gradually become thinner and shorter until they look like vellus hairs. This may be due to the growth of terminal hairs being influenced by hormones (e.g. androgens) while vellus hairs are not so influenced.

The progression of conditions such as AGA is for a gradual decrease in the number of terminal hairs over time. The terminal hairs may also gradually become thinner and shorter until they look like vellus hairs. It is surprising, therefore, that the current method can actually increase the number of hairs after 3 months. In addition to treatment of hair loss, the method of the present invention may be used for the stimulation of hair growth in areas not recognized as experiencing hair loss. As used herein, the term "hair growth" refers to an increase in number of terminal hairs present. Terminal hair counts can be conducted in a number of ways as known in the art. A non-limiting example is where the terminal hair is counted by trained and validated technicians who perform a computer-assisted count on macrophotographs. In brief, a target area on the scalp is chosen, the hair clipped and the scalp permanently marked with a single dot tattoo in the center in order to facilitate the exact positioning at each subsequent photo session. The macrophotography is performed using a preset camera with a macro lens and a stand that provides a constant reproduction ratio and electronic flashes that reproducibly illuminate the area to photograph. The images are taken in triplicate, centering the camera using the tattoo and the color slide films are processed at a central facility. The quality of the images is assessed and large transparencies are made of the best images. The terminal hairs on the target circle of the transparencies are then counted by the trained technicians.

In all embodiments of the invention, the disclosed PDT mediated methods may be repeated over time and preferably result in a 2% or more increase in the number of terminal hairs within 3 months.

In another aspect, the invention is directed to formulations or compositions comprising photosensitizers for treating lack of hair growth or a reduction or loss of existing hair with the methods of the invention. These compositions comprise an effective amount of photosensitizer, optionally with a pharmaceutically acceptable carrier or excipient, and may also be used to prevent or inhibit the development of hair growth reduction or hair loss. The invention includes pharmaceutical compositions targeted to hair follicles, the surrounding tissue, or tissues which feed hair follicles. In particular, formulations comprising photosensitizers conjugated to agents, which specifically target or bind appropriate scalp or skin tissues, hair follicles, or tissues and cells surrounding said hair follicles, are preferred for use in the methods of the invention. Compositions comprising conjugated or unconjugated photosensitizers are optionally formulated with agents suitable or preferred for application to the scalp, or other skin where hair growth is desired. Examples of such agents include pharmaceutically acceptable carriers or excipients.

The invention also provides for methods of using photosensitizer formulations and compositions in preparing an area of skin for PDT to increase the number of terminal hairs in said area, or to treat AGA, said methods comprising administering, preferably by topical administration, such formulations and compositions to said area.

In one set of preferred embodiments, the invention is practiced with a photosensitizer that is photoactivated by light of a wavelength from about 400 to about 900 nm. In another set of preferred embodiments of the invention, the treatment methods and compositions comprise the use of a particularly potent group of photosensitizers known as green porphyrins, which are described in detail in Levy et al., U.S. Pat. No. 5,171,749 issued Dec. 15, 1992, which is incorporated herein by reference. The term "green porphyrins" refers to porphyrin derivatives obtained by reacting a porphyrin nucleus with an alkyne in a Diels-Alder type reaction to obtain a mono-hydrobenzoporphyrin. In particular, green porphyrin compounds such as benzoporphyrin derivative mono-acid (BPD-MA), EA6, and B3 may be used in the invention. Two preferred members of the green porphyrin family are verteporfin (comprising the 4 enantiomers shown below) and QLT 0074.

BPD-MA$_C$

BPD-MA$_D$

BPD-MA$_C$

BPD-MA$_D$

QLT 0074

Additionally, the methods of the invention preferably comprise irradiation with visible light containing a wavelength absorbed by Gp.

The invention also provides methods of stimulating an increase in tissue levels of one or more growth factors or cytokines in cells present within skin tissue by the use of PDT. More particularly, the cytokines include, but are not limited to, interleukin-1-α, interleukin-1-β, and granulocyte-macrophage colony stimulating factor (GM-CSF). Without being bound by theory, it is believed that PDT mediated increases in pro-inflammatory cytokines play a role in inducing hair, particularly terminal hair, growth as described herein. The invention also provides for the use of such increases in the treatment of other conditions.

In another aspect, the invention provides for methods to determine the amount of increase in hair growth mediated by PDT. These methods may be practiced with any photosensitizer in various amounts or concentrations and with use of various irradiation regimens, including, but not limited to, those with variations in timing, radiation energy dose and/or rate, and wavelength of radiation. In one embodiment, such methods comprise a) administering a photosensitizer to skin exhibiting hair growth reduction or hair loss;
b) irradiating said skin with electromagnetic energy containing a wavelength absorbed by said photosensitizer to activate it; and
c) measuring the increase in hair growth, wherein an increase in hair growth in comparison to skin that has not been treated with both a) and b) can be determined. Preferably, the photosensitizer is one which absorbs activating radiation in the range of about 400 nm to about 800 nm and is administered by topical application. Said measuring can be by any means known to the skilled person, including, but not limited to, counting the number of terminal hairs, measuring hair weight, measuring hair density, and/or measuring hair shaft diameter, most preferably by counting the number of terminal hairs. Preferably, the skin that has not been treated has not been treated with one of a) and b).

BRIEF DESCRIPTION OF THE DRAWINGS

FIG. 1 shows photographs taken over time of a representative untreated control C57BL/6 mouse from an experiment examining the effect of photodynamic therapy (PDT) treatment of mice with alopecia of unknown etiology (Example 1). FIGS. 1.1 to 1.4 shows a control mouse with a worsening of the alopecic condition over the experimental period of 28 days.

FIG. 2 shows photographs taken over time of a representative PDT treated C57BL/6 mouse from the experiment examining the effect of PDT treatment on mice with alopecia of unknown etiology (Example 1). FIGS. 2.1 to 2.4 demonstrate that the PDT treatment over the experimental period of 28 days resulted in impressive hair growth in the alopecic patches.

DETAILED DESCRIPTION

Briefly stated, the invention provides methods and compositions for stimulating hair growth utilizing photodynamic therapy (PDT) treatment. For example, one aspect of the invention includes methods for inducing or stimulating hair growth in animals characterized by reduction or loss of hair. A sample method would comprise: (a) administering an effective and/or sufficient amount of a photosensitizer capable of penetrating into target skin to result in an effective or desired degree of biodistribution; (b) irradiating the target skin with light comprising one or more wavelength capable of activating said photosensitizer for a time period sufficient to activate the photosensitizer; and optionally (c) repeating (a) and (b) as necessary or desired to elicit a desired level of hair growth. Such hair growth would be the desired therapeutic response in the majority of cases. PDT treatment of hair loss has the advantage that it obviates the need for daily administration of a drug.

The present invention may be used with any subject, vertebrate or invertebrate, capable of hair growth. Preferably, the invention is applied to skin tissue exhibiting, or suspected of, hair growth reduction or hair loss. Preferred subjects include mammals, with human subjects being particularly preferred. The present invention is useful for treating subjects, particularly humans, suffering from AGA.

After administration, the photosensitizer will be present in hair follicles and the surrounding tissues and cells for photoactivation. Irradiation with electromagnetic energy, preferably with light of appropriate wavelength and intensity, will be applied using an appropriate light source, thereby activating the photosensitizer to stimulate and/or restore hair growth. Appropriate activation energy sources can be any that is suitable. For example, sunlight or other ambient sources may be used but preferred for use are devices which allow a controlled energy dose to be delivered. By "stimulating" or "restoring" hair growth, all manner of inducing, reviving, renewing, replacing or otherwise activating hair growth are included. Preferably, the irradiation is with visible light or comprises a wavelength of visible light.

Any suitable photosensitizing agent or mixture of agents may be used herein. Generally, these will absorb radiation in the range of from about 380 nm to about 900 nm. Preferred are those which absorb radiation in the range 400 nm to 800 nm. Those that absorb radiation in the range of from 600 nm to 750 nm are even more preferred. As used herein, "photosensitizer" or "photosensitizing agent" preferably means a chemical compound which, when contacted by radiation of a certain wavelength, forms singlet oxygen. More preferred is a photosensitizer that is nontoxic to humans or is capable of being formulated in a nontoxic composition. Even more preferred is a chemical compound that is also nontoxic in its photodegraded form after administration to a subject. A photosensitizer may be defined as a substance that absorbs electromagnetic radiation, most commonly in the visible spectrum, and releases it as another for of energy, most commonly as reactive oxygen species and/or as thermal energy.

The formulations and methods of the invention generally relate to administering a photosensitizer, such as a green porphyrin, to a subject undergoing PDT for alopecia. In one embodiment, the methods of the invention are used to stimulate and/or restore hair growth after initial diagnosis of a subject as suffering from hair loss, such as that resulting from AGA. In another embodiment, the methods of the invention follow other treatments for alopecia, including PDT, as a form of maintenance therapy to prevent appreciable hair loss and/or maintain hair growth. The latter may be used to prevent or inhibit the re-occurrence of alopecia.

The present invention also provides methods for causing an increase in the number of terminal hairs by use of PDT in the area in which an increase in the number of terminal hairs is desired and administering at least one secondary treatment that causes an increase in the number of terminal hairs within the treatment area, wherein the secondary treatment is not photodynamic therapy. The non-photodynamic treatment can be any suitable regimen, but is preferably one that increases terminal hair numbers via a different method of action from PDT treatment. For example, a local treatment or a systemic treatment. Preferably, the secondary treatment is selected from 5-alpha reductase inhibitors, minoxidil, hair transplantation, scalp reduction, and combinations thereof. More preferably, the secondary treatment is selected from 5-alpha reductase inhibitors, minoxidil, and combinations thereof. For example, Rogaine™ or Propecia™ maybe utilised in combination with PDT treatment(s). For example, a patient may receive one or several PDT treatments, but also use Rogaine™ or Propecia™ as recommended.

One preferred method herein thus comprises:
a) topically administering photosensitizer to a target skin tissue,
b) irradiating the target tissue with electromagnetic radiation of a wavelength appropriate to activate the photosensitizer, and
c) administering at least one, non-photodynamic, treatment that causes an increase in the number of terminal hairs within the treatment area.

The non-photodynamic treatment can be administered at any suitable time, before, concurrently or after the PDT. It is preferred that the non-photodynamic treatment is selected from 5-alpha reductase inhibitors, minoxidil, and combinations thereof.

If the non-photodynamic treatment is minoxidil it is preferably used as a topical solution. Preferably the solution is administered from 1 to 4 times daily, more preferably twice daily. The solution can be any suitable strength but is preferably from about 1% to about 10%, more preferably about 2% or about 5%.

If the non-photodynamic treatment is 5-alpha reductase inhibitors it is preferably administered orally. Preferred 5-alpha reductase inhibitor is finasteride. Finasteride is preferably administered as a 1 mg oral table and is preferably taken once a day.

The methods of the invention can be used to stimulate hair growth in any situation in which additional hair growth is desired. In particular, the methods of the invention will be useful when the subject has experienced loss of hair associated with a variety of conditions, including, but not limited to the following: anagen effluvium, drug-induced alopecia, radiotherapy, poisoning, diffuse alopecia areata, alopecia areata, loose anagen syndrome, postoperative occipital alopecia, syphilis, traction alopecia, tricholtillomania tinea capitis, telogen effluvium, telogen gravidarum, chronic telogen effluvium, early androgenentic alopecia, iron deficiency, malnutrition/malabsorption, hypothyroidism, hyperthyroidism, systemic lupus erythematosus, chronic renal failure, hepatic failure, advanced malignancy, viral or bacterial infection and androgenetic alopecia. In particular, the methods of the invention are useful for restoration of hair loss in androgenetic alopecia, alopecia areata, drug-induced alopecia (for example following chemotherapy treatment for cancer) and hair loss due to radiation treatment.

If the condition being treated is alopecia areata, preferably the photosensitizer pro-drug 5-ALA is not used for topical administration unless combined with at least one penetration enhancer that promotes the distribution of the drug within the hair follicles.

After administration of the photosensitizer, sufficient time is permitted to elapse for the compound to be taken up by the hair follicles and/or the surrounding tissues and cells. This time for uptake may be varied according to various parameters, including but not limited to the photosensitizer administered, the route of administration, the physiology of the subject and of the tumor cells, and the artisan's skill and experience. With green porphyrins, for example, the elapsed time may be from less than about one minute to more than three hours, preferably from one minute to three hours, and more preferably from 10 to 60 minutes. The cells, or tissues containing them, are then irradiated at the wavelength of maximum absorbance of the photosensitizer. In the case of BPDs, the wavelength is usually between about 550 and 700 nm, as discussed above. In particular, red light is advantageous because of its relatively lower energy and the resulting lack of toxicity it poses to normal tissue.

Without being bound by theory, it is believed that the methods of the invention stimulates an increase in tissue levels of one or more growth factors and/or cytokines in the treated tissues which then directly, or through other biochemical pathways, stimulate resting hair follicles to enter the anagen (growth) phase. In PDT-mediated hair growth it is believed that pro-inflammatory cytokines, such as interleukin-1-alpha, interleukin-1-beta, or granulocyte-macrophage colony stimulating factor (GM-CSF), play a role in inducing hair, particularly terminal hair, growth as described herein. Pro-inflammatory cytokines, such as IL-1 and GM-CSF, are known to have a wide range of effects within tissues. These actions may include stimulating the production of various biochemical mediators, up-regulating the expression of specific cell surface receptors and triggering the activation and tissue infiltration of pro-inflammatory cell types including neutrophils and macrophages. It is particularly surprising that IL-1-α can cause an increase in the number of terminal hairs since there is a body of evidence that suggests IL-1 induces hair loss rather than hair growth (see, for example, *Dermatology* 1995;191:273-275 Hoffiann et al; *Eur J Dermatol* 1998;8:475-7 Hoffmann et al; *Lymphokine & Cytokine Research* Vol.12, Number 4, 1993 Harmon et al).

Cells capable of producing such cytokines include keratinocytes, dermal fibroblasts, and dermal papilla cells. Consequently, the present invention also relates to a method of causing an increase in the number of terminal hairs with photodynamic therapy said method comprising inducing pro-inflammatory cytokines, particularly granulocyte-macrophage colony stimulating factor and/or interleukin-1-α (IL-1-α).

Therefore, the present invention also relates to a method of causing an increase in the number of terminal hairs by increasing the levels of pro-inflammatory cytokines in the target area. The method comprises treating the area with photodynamic therapy wherein said photodynamic therapy causes an increase in the levels of pro-inflammatory cytokines in the area where hair growth is desired. Preferably the PDT treatment causes an increase in granulocyte-macrophage colony stimulating factor, interleukin-1-β (IL-1-β), and/or interleukin-1-α (IL-1-α).

The present method provides at least 2% increase in the numbers of terminal hairs within 3 months of the PDT treatment. Preferably, the present invention provides a 3% or more increase, more preferably a 4% or more increase, in the numbers of terminal hairs within 3 months. The numbers of terminal hairs on a particular subject can be assessed by any means known to the skilled person, such as the validated method described in "Photographic Documentation of Hair Growth in Androgenetic Alopecia" (D. Canfield, *Dermatologic Clinics*, Vol. 14 No. 4 (October 1996)713-721).

In one embodiment, the method can comprise:
(a) assessing the numbers of terminal hairs in an area of skin;
(b) administering an effective amount of a photosensitizer to said area;
(c) irradiating the area with activation energy comprising one or more wavelength capable of activating said photosensitizer for a time period sufficient to activate the photosensitizer; and
(d) optionally repeating (b) and (c);
(e) assessing the numbers of terminal hairs according to the above mentioned method 3 months from the date of first treatment.

The method preferably produces at least a 2%, more preferably at least a 3%, and even more preferably at least a 4% increase in the numbers of terminal hairs as assessed within 3 months.

The compositions and methods of the present invention provide a useful PDT treatment to treat, and/or prevent or inhibit re-occurrence of, alopecia. The following describes exemplary photosensitizers, compositions and formulations of the present invention and their clinical application. Experimental data also are presented and described.

Photosensitizers

A listing of photosensitive chemicals for use in the present invention may be found in Kreimer-Bimbaum, Sem. Hematol. 26:157-73, 1989 (incorporated herein by reference) and in Redmond and Gamlin, Photochem. Photobiol. 70 (4): 391-475 (1999). The invention may be practiced with a variety of synthetic and naturally occurring photosensitizers, including, but not limited to, pro-drugs such as the pro-porphyrin 5-aminolevulinic acid (ALA) and derivatives thereof such as aminolevulinic acid esters, porphyrins and porphyrin derivatives e.g. chlorins, bacteriochlorins, isobacteriochlorins, phthalocyanine and naphthalocyanines and other tetra- and poly-macrocyclic compounds, and related compounds (e.g. pyropheophorbides, sapphyrins and texaphyrins) and metal complexes such as, but not limited to, tin, aluminum, zinc, lutetium, tin ethyl etiopurpurin (SnET2). Tetrahydrochlorins, purpurins, porphycenes, and phenothiaziniums are also within the scope of the invention. Some examples of suitable compounds include, but are not limited to, those described in U.S. Pat. Nos. 6,462,192; 6,444,194; 6,376,483; WO-A-03/028628; WO-A-03/028629; WO-A-02/096417; and WO-A-02/096366, all of which are herein incorporated by reference.

Preferably the photosensitizers herein are selected from pro-porphyrins, porphyrins, and mixtures thereof. Some examples include aminolevulinic acid such as Levulan™, aminolevulinic acid esters such as described in WO-A-02/10120 and available as Metvix™, Hexvix™ and Benzvix™, di-hydro or tetra-hydro porphyrins such as described in described in EP-A-337,601 or WO-A-01/66550 and available as Foscan™ (temoporfin), porfimer sodium (available as Photofrin™), Visudyne™, benzoporphyrin derivatives (which are described in more detail below), and mixtures thereof.

In preferred embodiments of the invention, the photosensitizer is selected from a particularly potent group of photosensitizers known as green porphyrins, which are described in detail in U.S. Pat. No. 5,171,749 (incorporated herein by reference). The term "green porphyrins" refers to porphyrin derivatives obtained by reacting a porphyrin nucleus with an alkyne in a Diels-Alder type reaction to obtain a mono-hydrobenzoporphyrin. Such resultant macropyrrolic compounds are called benzoporphyrin derivatives (BPDs), which is a synthetic chlorin-like porphyrin with various structural analogues, as shown in U.S. Pat. No. 5,171,749. Typically, green porphyrins are selected from a group of tetrapyrrolic porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B). Metallated forms of a Gp, in which a metal cation replaces one or two hydrogens in the center of the ring system, may also be used in the practice of the invention. The preparation of the green porphyrin compounds useful in this invention is described in detail in U.S. Pat. No. 5,095,030 (hereby incorporated by reference).

Preferably, the BPD is a benzoporphyrin derivative diester di-acid (BPD-DA), mono-acid ring A (BPD-MA), mono-acid ring B (BPD-MB), or mixtures thereof. These compounds absorb light at about 692 nm wavelength and have improved tissue penetration properties. The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. A number of other BPD B-ring derivatives may also be used in the present methods. These derivatives have the following general formula:

wherein; $R^5$ is vinyl, $R^1$ and $R^6$ are methyl, and n is 2. $X_1$, $X_2$, and $X_3$ are listed in the tables below:

TABLE 1

Hydrophilic BPD B-ring analogs

| Drug | $X_1$ | $X_2$ | $X_3$ |
| --- | --- | --- | --- |
| QLT0061 | COOH | COOH | COOH |
| QLT0077 | $CONH(CH_2)_2N^+(CH_3)_3I^-$ | $CONH(CH_2)_2N^+(CH_3)_3I^-$ | $COOCH_3$ |
| QLT0079 | $CONH(CH_2)_2N^+(CH_3)_2((CH_2)_3CH_3$ | $CONH(CH_2)_2N^+(CH_3)_2((CH_2)_3CH_3)$ | $COOCH_3$ |
| QLT0086 | $CONHCH(COOH)CH_2COOH$ | $CONHCH(COOH)CH_2COOH$ | $COOCH_3$ |
| QLT0092 | $CONH(CH_2)_2NH(CH_3)_2$ $CF_3COO^-$ | $CONH(CH_2)_2NH(CH_3)_2$ $CF_3COO-$ | $COOCH_3$ |
| QLT0094 | $CONHCH_2COOH$ | $CONHCH_2COOH$ | $CONHCH_2COOH$ |

TABLE 2

Lipophilic BPD B-ring analogs

| Drug | X1 | X2 | X3 |
| --- | --- | --- | --- |
| QLT0060 | $CO(O(CH_2)_2)0H$ | $CO(O(CH_2)_2)0H$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Preferred photosensitizers are the benzoporphyrin derivative mono-acid (BPD-MA), QLT0074 (as set forth in U.S. Pat. No. 5,929,105 referred to therein as A-EA6) and B3 (as set forth in U.S. Pat. No. 5,990,149). Most preferably the photosensitizer is QLT0074 which has the structure:

Additionally, the photosensitizers used in the invention may be conjugated to various ligands to facilitate targeting. These ligands include receptor-specific ligands as well as immunoglobulins and fragments thereof. Preferred ligands include antibodies in general and monoclonal antibodies, as well as immunologically reactive fragments of both.

Dimeric forms of the green porphyrin and dimeric or multimeric forms of green porphyrin/porphyrin combinations can be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins. Combinations of two or more photosensitizers may also be used in the practice of the invention.

In addition to the above mentioned preferred photosensitizing agents, additional examples of photosensitizers useful in the invention include, but are not limited to, green porphyrins disclosed in U. S. Pat. Nos. 5,283,255, 4,920,143, 4,883,790, 5,095,030, and 5,171,749; and green porphyrin derivatives, discussed in U.S. Pat. Nos. 5,880,145 and 5,990,149. Several structures of typical green porphyrins are shown in the above cited patents, which also provide details for the production of the compounds.

A preferred photosensitizer for use in the present invention will satisfy the following general criteria: 1) it is capable of entry into the target hair follicles and/or the surrounding tissues and cells; and 2) irradiation, preferably with light (and more preferably with visible light), results in the stimulation of and/or restoration of hair growth.

Suitable photosensitizer formulations for the practice of the invention include those appropriate for administration of therapeutic compounds in vivo. Additionally, other components may be incorporated into such formulations. These include, for example, visible dyes to facilitate visualization or imaging of the formulation or various enzymes to facilitate the access of a photosensitizing compound to target sites.

Formulations

The photosensitizers of the invention may be formulated into a variety of compositions. These compositions may comprise any component that is suitable for the intended purpose, such as conventional delivery vehicles and excipients including isotonising agents, pH regulators, solvents, solubilizers, dyes, gelling agents and thickeners and buffers and combinations thereof. Pharmaceutical formulations suitable for use with the instant photosensitizers can be found, for instance, in *Remington's Pharmaceutical Sciences*. Preferred formulations herein comprise pharmaceutical excipients or carriers capable of directing the photosensitizer to the area of hair growth reduction or hair loss. Suitable excipients for use with photosensitizers include water, saline, dextrose, glycerol and the like.

Typically, the photosensitizer is formulated by mixing it, at an appropriate temperature, e.g., at ambient temperatures, and at appropriate pHs, and the desired degree of purity, with one or more physiologically acceptable carriers, i.e., carriers that are nontoxic at the dosages and concentrations employed. Generally, the pH of the formulation depends mainly on the particular use, and concentration of photosensitizer, but preferably ranges anywhere from about 3 to about 8. Preferably, the photosensitizer is maintained at a pH in the physiological range (e.g., about 6.5 to about 7.5). The presence of salts is not necessary, and, therefore the formulation preferably is not an electrolyte solution.

The formulations herein preferably comprise a skin-penetration enhancer. Any skin-penetration enhancer suitable for aiding the delivery of the photosensitizing agent can be used herein. A list of skin-penetration enhancers can be found in "Pharmaceutical Skin Penetration Enhancement" (1993) Walters, K. A., ed.; Hadgraft, J., ed—New York, N.Y. Marcel Dekker and in "Skin Penetration Enhancers cited in the Technical Literature" Osbourne, D. W. Pharmaceutical Technology, November 1997, pp 59-65, both of which are incorporated herein by reference. Preferred for use in the formulations herein are hydrophobic skin-penetration enhancers.

Preferred skin-penetration enhancers are selected from glycol ethers, fatty acids, fatty acid esters, glycol esters, glycerides, azones, polysorbates, alcohols, dimethylsulfoxide, and mixtures thereof. Preferred skin-penetration enhancers for use herein include, but are not limited to, diethylene glycol monoethyl ether (Transcutol®), Oleyl alcohol, Oleic acid, Azone (Laurocapram or 1-n-Dodecyl azacycloheptan-2-one), Propylene glycol mono- and diesters of fats and fatty acids (e.g. propylene glycol monocaprylate, propylene glycol monolaurate), Triglycerides and lipids (e.g. linoleic acid), Macrogolglycerides or Polyethylene glycol glycerides and fatty esters (e.g. stearoyl macrogolglycerides, oleoyl macrogolglycerides, lauroyl macrogolglycerides, Oleyl macrogol-6-glycerides, Lauroyl macrogol-6 glycerides), Glycerides and fatty acid esters of polyethylene glycol (e.g. caprylocaproyl macrogolglycerides, capryl-caproyl macrogolglycerides, oleoyl macrogol glycerides), Polyoxyl 40 Hydrogenated Castor Oil (Cremophor RH 40), Polysorbate 80 (Tween 80), Dodecylazacycloheptanone, SEPA® such as described in U.S. Pat. No. 4,861,764 (e.g. 2-n-nonyl-1,3-dioxolane), and mixtures thereof. More preferred is diethylene glycol monoethyl ether (available from Gattefosse under the tradename Transcutol).

It is preferred that the formulations comprise from about 0.1% to about 99%, preferably from about 0.1% to about 90%, more preferably from about 5% to about 90%, even more preferably from about 15% to about 75%, by weight of skin penetration enhancer.

It is preferred that the ratio of photosensitizer to skin-penetration enhancer is from about 1:20 to about 1:10000, more preferably from about 1:60 to 1:300, on the basis of percentages by weight of total composition.

It is preferred that the photosensitizer is solubilised, especially when the photosensitizer is hydrophobic. One method of solubilising certain photosensitizers, including green porphyrins, is by formulation in liposomes. An alternative may be to solubilise the photosensitizer in cyclodextrins or cyclodextrin derivatives. Preferred are partially etherified cyclodextrin, the ether substituents of which are hydroxyethyl, hydroxypropyl or dihydroxypropyl groups. However, appropriate cyclodextrins should be of a size and conformation appropriate for use with the photosensitizing agents disclosed herein.

Other methods suitable for solubilising certain photosensitizers include the use of a solvent acceptable for use in the treatment of skin tissues and cells such as, but are not limited to, DMSO (dimethylsulfoxide), polyethylene glycol (PEG) or any other solvent. It is preferred that the formulations herein comprise a solubilizer. Some solubilizers are also penetration enhancers and it is preferred that the formulations herein comprise a penetration enhancer that is also a solubilizer for the photosensitizer. Preferably the solubilizer is selected from glycol ethers, polyethylene glycol, polyethylene glycol derivatives, propylene glycol, propylene glycol derivatives, polysorbates (e.g. Tween™), fatty alcohols, aromatic alcohols, propylene glycol, glycerols, oils, surfactants, glucosides, and mixtures thereof. More preferably the solubilizer is selected from diethylene glycol monoethyl ether (Transcutol®), polyethylene glycol of average molecular weight from 100 to 5000, triethylene glycol, tetraethylene glycol, pentaethylene glycol, hexaethylene glycol, septaethylene glycol, octaethylene glycol, propylene glycol, propylene glycol mono- and diesters of fats and fatty acids (e.g. propylene glycol monocaprylate, propylene glycol monolaurate), benzyl alcohol, glycerol, oleyl alcohol, mineral oil, lanolin/lanolin derivatives, petrolatum or other petroleum products suitable for application to the skin, propylene glycol mono- and diesters of fats and fatty acids, macrogols, macrogolglycerides or polyethylene glycol glycerides and fatty esters (e.g. stearoyl macrogolglycerides, oleoyl macrogolglycerides, lauroyl macrogolglycerides, linoleoyl macrogolglycerides), ethoxylated castor oil (e.g. Cremophor—a polyoxyl hydrogenated castor oil), C6-C30 triglycerides, natural oils, glucosides (e.g. cetearyl glucoside), surfactants, and mixtures thereof. More preferable the solubilizer is selected from diethylene glycol monoethyl ether (Transcutol®), oleyl alcohol, and mixtures thereof.

It is preferred that the formulations herein comprise from about 0.1% to about 99%, more preferably from about 1% to about 75%, by weight of solubilizer.

It is preferred that the formulations have a viscosity at 20° C. of from about 50 cps to about 50000 cps, more preferably from about 500 cps to about 40000 cps, even more preferably from about 5000 cps to about 30000 cps. Should the viscosity need to be adjusted it can be done by means of a viscosity modifying agent. Preferred viscosity modifiers are selected from polyethylene glycols, acrylic acid-based polymers (carbopol polymers or carbomers), polymers of acrylic acid crosslinked with allyl sucrose or allylpentaerythritol (carbopol homopolymers), polymers of acrylic acid modified by long chain (C10-C30) alkyl acrylates and crosslinked with allylpentaerythritol (carbopol copolymers), poloxamers also known as pluronics (block polymers; e.g. Poloxamer 124, 188, 237, 338, 407), waxes (paraffin, glyceryl monostearate, diethylene glycol monostearate, propylene glycol monostearate, ethylene glycol monosterate, glycol stearate), hard fats (e.g. Saturated C8-C 18 fatty acid glycerides), xantham gum, polyvinyl alcohol, solid alcohols, and mixtures thereof.

In preferred embodiments the formulation contain one or more PEGs. It is preferred that the formulation comprises at least one PEG of average molecular weight about 2000 or less, preferably about 1500 or less, preferably about 1000 or less, preferably about 800 or less, preferably about 600 or less, preferably about 500 or less, preferably about 400 or less. It is preferred that the formulation comprises at least one PEG of average molecular weight about 3000 or more, preferably about 3350 or more, preferably about 3500 or more. It is preferred that the formulation comprises a mixture of PEG's. More preferably, one PEG has an average molecular weight of about 800 or less and one PEG has an average molecular weight of 3000 or more.

A preferred formulation for use in the present invention comprises photosensitizer (especially green-porphyrins), low molecular weight PEG such as PEG200, diethylene glycol monoethyl ether (Transcutol®), high molecular weight PEG such as PEG3350 and fatty alcohol such as oleyl alcohol.

The formulation herein may comprise a variety of other components. Any suitable ingredient may be used herein but typically these optional component will render the formulations more cosmetically acceptable or provide additional usage benefits. Some examples of preferred optional ingredients include, but are not limited to, emulsifiers, humectants, emollients, surfactants, oils, waxes, fatty alcohols, dispersants, skin-benefit agents, pH adjusters, dyes/colourants, analgesics, perfumes, preservatives, and mixtures thereof.

Examples of suitable preservatives include but are not limited to parabens, benzyl alcohol, quaternium 15, imidazolidyl urea, disodium EDTA, methylisothiazoline, alcohols, and mixtures thereof. Examples of suitable emulsifiers include but are not limited to waxes, sorbitan esters, polysorbates, ethoxylated castor oil, ethoxylated fatty alcohols, macrogolglycerides or polyethylene glycol glycerides and fatty esters (e.g. stearoyl macrogolglycerides, oleoyl macrogolglycerides, lauroyl macrogolglycerides), esters of saturated fatty acids (e.g. diethylene glycol parmitostearate), macrogols of cetostearyl ether (e.g. macrogol-6-cetostearyl ether), polymers of high molecular weight, crosslinked acrylic acid-based polymers (carbopols or carbomers), and mixtures thereof. Examples of suitable emollients include but are not limited to propylene glycol dipelargonate, 2-octyldodecyl myristate, non-polar esters, triglycerides and esters (animal and vegetable oils), lanolin, lanolin derivatives, cholesterol, glucosides (e.g. cetearyl glucoside), pegylated lanolin, ethoxylated glycerides, and mixtures thereof. Examples of suitable surfactants include but are not limited to sorbitan esters, polysorbates, sarcosinates, taurate, ethoxylated castor oil, ethoxylated fatty alcohols, ethoxylated glycerides, caprylocaproyl macrogol-8 glycerides, polyglyceryl-6 dioleate, and mixtures thereof. Examples of suitable oils include but are not limited to propylene glycol monocaprylate, medium chain triglycerides (MCT), 2-octyldodecyl myristate, cetearyl ethylhexanoate, and mixtures thereof. Examples of suitable fatty alcohols include but are not limited to cetostearyl alcohol, cetyl alcohol, stearyl alcohol, and mixtures thereof. Also useful in the formulations herein are lipids and triglycerides (e.g. concentrates of Seed Oil Lipids, Concentrates of Marine Oil Lipids, high purity triglycerides and esters), alkyl ether sulfates, alkyl polyglycosides, alkylsulfates, amphoterics cream bases, and mixtures thereof.

Preparation of dry formulations that are reconstituted immediately before use also is contemplated. The preparation of dry or lyophilized formulations can be effected in a known manner, conveniently from the solutions of the invention. The dry formulations of this invention are also storable. By conventional techniques, a solution can be evaporated to dryness under mild conditions, especially after the addition of solvents for azeotropic removal of water, typically a mixture of toluene and ethanol. The residue is thereafter conveniently dried, e.g. for some hours in a drying oven.

The method herein is targeted to hair follicles and/or surrounding tissues and cells as a treatment for alopecia. The photosensitizer containing preparations of the invention may be administered systemically or locally and may be used alone or as components of mixtures. Preferably the administration is local. The route of administration for the photosensitizer may be topical, intradermal, intravenous, oral, or by use of an implant. Preferably the route of administration is topical. For example, green porphyrins may be administered by means including, but not limited to, topical lotions, topical creams, topical pastes, topical suspensions, intravenous injection or infusion, oral intake, or local administration in the form of intradermal injection or an implant. Additional routes of administration are subcutaneous, intramuscular, or intraperitoneal injections of the photosensitizers in conventional or convenient forms.

For topical formulations (such as ointments) to be applied to the surface of the skin, the concentration of the photosensitizer in the excipient preferably ranges from about 0.001 to about 10% w/w, and more preferably from about 0.005 to about 5% w/w, and even more preferably between about 0.01 to about 1% w/w. Particularly preferred is the use of about a 0.2% w/w topical formulation.

When administered topically, it is preferred that the area to be treated be massaged after application of the photosensitizer. While not wishing to be bound by theory, it is believed that the massage aids in the penetration and distribution of photosensitizer in the target tissue.

The particular concentration of a given photosensitizer should be adjusted according to its photosensitizing potency.

Suitable isotonising agents are preferably nonionic isotonising agents such as urea, glycerol, sorbitol, mannitol, aminoethanol or propylene glycol as well as ionic isotonising agents such as sodium chloride. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 milliosmol (mOsm), conveniently 300+10% mOsm. It should be borne in mind that all components of the solution contribute to the osmolarity. The nonionic isotonising agent, if present, is added in customary amounts, i.e., preferably in amounts of about 1 to about 3.5 percent by weight, preferably in amounts of about 1.5 to 3 percent by weight.

Administration of Photosensitizers

As noted above, the treatment methods of the invention are targeted to hair follicles and/or surrounding tissues and cells as a treatment for alopecia. The photosensitizer containing preparations of the invention may be administered systemically or locally and may be used alone or as components of mixtures. The route of administration for the photosensitizer may be topical, intravenous, oral, or by use of an implant. For example green porphyrins may be administered by means including, but not limited to, topical preparations, intravenous injection or infusion, oral intake, or local administration in the form of intradermal injection or an implant. Additional routes of administration are subcutaneous, intramuscular, or intraperitoneal injections of the photosensitizers in conventional or convenient forms.

In particular, topical delivery of photosensitizers is preferred, while injection may also be used when desired. For topical administration, the photosensitizers may be in standard topical formulations and compositions including lotions, suspensions or pastes. Oral administration of suitable formulations may also be appropriate in those instances where the photosensitizer may be readily administered to the hair follicle and/or surrounding tissues or cells via this route. A preferred method of administration is to apply the photosensitizer topically in an excipient containing solubilizing agent, such as Cremophor or corn glycerides, and to wash the treatment area within about an hour (such as, but not limited to, after about 10, about 15, about 20, about 30, about 45, or about 60 minutes) with the excipient to remove excess drug from the surface of the skin.

The dose of photosensitizers may be optimized by the skilled artisan depending on factors such as, but not limited to, the photosensitizer chosen, the physical delivery system in which it is carried, the individual subject, and the judgment of the skilled practitioner. It should be noted that the various parameters used for effective PDT in the invention are interrelated. Therefore, the dose should also be adjusted with respect to other parameters, for example, fluence, irradiance, duration of the light used in PDT, and time interval between administration of the dose and the therapeutic irradiation. All of these parameters may be readily adjusted using routine experimentation to produce a desired level of alopecia treatment without causing significant damage to the surrounding tissue. With photosensitizers, for example, the form of administration, such as in liposomes or when coupled to a target-specific ligand, such as an antibody or an immunologically active fragment thereof, is one factor considered by a skilled artisan.

Depending on the specificity of the preparation, smaller or larger doses of photosensitizers may be needed. For compositions which are highly specific to the target skin tissues and cells, such as those with the photosensitizer conjugated to a highly specific monoclonal antibody preparation or specific receptor ligand, dosages in the range of 0.005-10 mg/kg of body weight are suggested for systemic administration. For compositions which are less specific to the target, larger dosages, up to 1-20 mg/kg, may be desirable. The potency of the photosensitizer also determines the dosage, with less required for highly potent photosensitizers, and more for photosensitizers with less potency. The preferred range for use in mice is from about 0.05 mg/kg to about 20 mg/kg. The useful range in humans for the photosensitizer will be lower than mice, such as from about 0.005 mg/kg to about 4 mg/kg, and preferably from about 0.05 to about 2.0 mg/kg.

For topical formulations (such as ointments) to be applied to the surface of the skin, the concentration of the photosensitizer in the excipient can range from about 0.001 to about 10% w/w, and more preferably from about 0.005 to about 5% w/w (or about 0.05 to about 1% w/w), and even more preferably between about 0.1 to about 1% w/w. Particularly preferred is the use of a 0.2% (or about 0.2) w/w topical formulation. The foregoing ranges are merely suggestive in that the number of variables with regard to an individual treatment regime is large and considerable deviation from these values may be expected.

The skilled artisan is free to vary the foregoing concentrations so that the uptake and stimulation/restoration parameters are consistent with the therapeutic objectives disclosed above. The concentration of a particular photosensitizer to use in a topical formulation can easily be determined by performing a dose ranging study similar to the one outlined in the Examples below.

Each photosensitizer requires activation with an appropriate wavelength(s) of electromagnetic radiation. As such, the methods of the invention may be conducted with any irradiation, preferably with light, which activates the photosensitizer used. Preferably, the irradiation contains one or more wavelength which is capable of penetrating the skin to activate the photosensitizer used. The wavelength(s) of radiation or light useful in the invention depends on the activation range of the photosensitizer used as part of the treatment method. Wavelengths of about 380-900 nanometers (nm) are preferred, depending upon the photosensitizer and upon the depth of tissue penetration desired. More preferred are wavelengths from about 400 to about 900 nm, most preferred from about 400 to about 700 nm. For example, BPD-MA, a green porphyrin derivative, can be activated by red and blue light as well as ambient light containing wavelengths from 400-900 nm. Light having a wavelength shorter than 400 nm is acceptable, but not preferred because of the potentially damaging effects of UVA light.

Any appropriate activation energy source, depending on the absorption spectrum of the photosensitizer, may be used for photosensitizer activation. Preferred sources include, but are not limited to, lasers, light emitting diodes (LED), incandescent lamps, arc lamps, standard fluorescent lamps, U.V. lamps, and combinations thereof. More preferred are lasers, light emitting diodes, and combinations thereof Alternatively any convenient source of activation energy having a component of wavelengths that are absorbed by the photosensitizer may be used, for example, an operating room lamp, or any bright light source, including sunlight. Wavelengths in the ultraviolet range should, however, may be avoided because of their mutagenic potential. Therefore, and in some embodiments of the invention, the activation energy used for the methods herein is not in the ultraviolet range. Commercially available activation energy sources include CureLight™ (available from Photocure ASA, Oslo, Norway), BLU-U™ (available from DUSA, Wilmington, Mass., USA), PDT Laser (available from Diomed, Andover, Mass., USA), Ceralas™ (available from Biolitec AG, Jena, Germany), and Q-Beam & Quanta-med (Quantum Devices Inc., Barneveld, Wis., USA).

The activation energy dose administered during the PDT treatment contemplated herein can vary as necessary. Preferably, for photosensitizers of high potency, such as green porphyrins, the dosage of the light is about 5-50 $J/cm^2$ for systemically-delivered drug and about 25-200 $J/cm^2$ for topically-delivered photosensitizers. It is generally preferred that the total dose of the irradiation should generally not exceed 200 $J/cm^2$, or more preferably not exceed 100 $J/cm^2$. Preferred doses can range between about 0.01 $J/cm^2$ to about 200 $J/cm^2$, more preferably 0.1 $J/cm^2$ to about 100 $j/cm^2$. For example, about 25, about 50, about 75, about 100, about 125, about 150, or about 175 $J/cm^2$. More preferred doses range from about 25 $J/cm^2$ to about 100 $J/cm^2$. Even more preferred doses range from about 40 $J/cm^2$ to about 80 $J/cm^2$, especially about 50 $J/cm^2$ to about 75 $J/cm^2$. Increases in irradiance will generally decrease the light exposure times. Generally, a higher dose of photosensitizer will decrease the light dose required to exert a therapeutic effect.

Normally, the intensity of the light source should not exceed about 600-1000 mW/cm$^2$. Irradiances between about 10 and about 400 mW/cm$^2$, and more preferably between about 25 and about 100 mW/cm$^2$ are preferred.

Normally, the irradiation lasts from about 10 seconds to about 4 hours, and preferably between about 5 minutes and 1 hour. Irradiation times of about 10, about 15, about 20, about 30, about 45, about 60, about 75, about 90, about 105, about 120, about 135, about 150, about 165 and about 180 minutes may be used.

While not wishing to be bound by theory, it is believed that different photosensitizers, different formulations, and different activation energies will require different parameters in order to cause hair growth. Such parameters can be determined by simple dose-ranging studies. For example, a suitable method could involve:

(a) taking a terminal hair count,
(b) applying the photosensitizing composition at various strengths,
(c) waiting for varying lengths of time,
(d) treating with various activation energy doses, and
(e) reassessing hair counts.

Alternatively, the study might involve some other methods of assessing hair growth such as (visual) assessment of the hair density, hair weight, and/or hair shaft diameter.

It is preferred that the present invention not involve a PDT dose that results in extensive cell death in the treatment area. PDT dose is determined by two factors, the amount of photosensitizer present and the amount of activation energy delivered. While not wishing to be bound by theory, it is believed that the mechanism by which PDT stimulates hair growth is through increasing the levels of pro-inflammatory cytokines. It is thought that these cytokines act through biochemical pathways to cause susceptible hair follicles to grow terminal hair. It is possible that there is a specific dose range where the PDT dose is high enough to increase the level of these pro-inflammatory cytokines but low enough to avoid unwarranted side-effects such as extensive cell death and the resultant tissue damage. In addition, as discussed above, it has been suggested that PDT could be used for hair removal and, while the inventors have not found that PDT aids hair removal and not wishing to be bound by theory, it is possible that at higher doses of PDT may affect the hair follicle in such a way that hair removal is aided while lower doses of PDT stimulates an increase in terminal hair numbers. As used herein, the term "low dose of PDT" refers to dose of PDT that don't result in extensive cell death.

It is preferred that the area to be treated have minimal hair coverage when the activation energy is applied. Therefore, if there is significant hair coverage of the area to be treated, it is preferred that the hair is cut short or shaved prior to energy application. While not wishing to be bound by theory, it is believed that, due to the fact that hair has a light shielding function, hair coverage can affect the energy dose that is delivered to the target area. Consequently, in order to more accurately deliver the correct light does it is preferred that there be little or no hair coverage. Alternatively, the shielding effect of the hair may be compensated for by changes to delivery of the activation energy.

The irradiation or light exposure used in the invention may be directed to a small or large area of the body or scalp depending on the patch to be treated. Treatment may be preceded with an assessment of the time of light exposure for the patient's minimal erythemal dose (MED) occurrence in order to avoid potential burning of the exposed skin.

The PDT may be a single treatment but it is preferred that the treatment is repeated. The frequency may vary. For example, the treatments could be daily, every two days, twice weekly, weekly, ever two weeks, twice monthly, every four weeks, monthly, every six weeks, every eight weeks, every two months, quarterly, twice annually, or annually, or other suitable time interval to stimulate hair growth or to maintain the prevailing condition. Preferably, the treatment is repeated at least once every six months. More preferably at least once every three months. Even more preferably at least once every two months.

The total number of treatments can range from one to as many as required. In cases where hair loss is observed, maintenance treatment on a regular basis may be initiated and sustained. It is preferred that the total number of treatments in any 3 month period be from 1 to 12, more preferably from 1 to 6, even more preferably from 2 to 3. Frequencies of 1, 2, 3, 4, 5, 6, or 12 times per 3 month period may also be used.

The time between administration of photosensitizer and administration of activation energy will vary depending on a number of factors. Activation energy delivery can take place at any suitable time following administration of photosensitizer as long as there is still photosensitizer present at the skin. Activation energy treatment within a period of about five minutes to about 6 hours after administration of the photosensitizer is preferred, with a range of 30 minutes to 4 hours being more preferred. Even more preferably the light is administered within a period of about 2 hours after administration of the photosensitizer. Photosensitizers that rapidly accumulate in target tissues can be activated soon after administration. Photosensitizers that are cleared from tissues quickly should be activated soon after accumulation in the target tissues.

Having now generally described the invention, the same will be more readily understood through reference to the following examples which are provided by way of illustration, and are not intended to be limiting of the present invention, unless specified.

EXAMPLE 1

Figure 11:
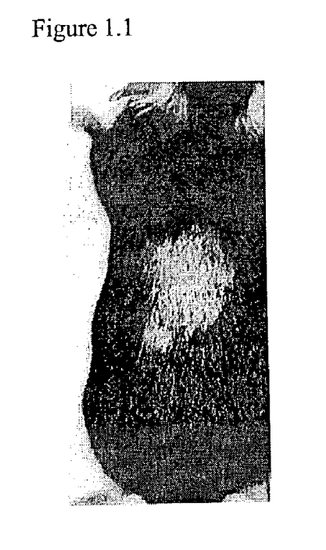
Figure 12:
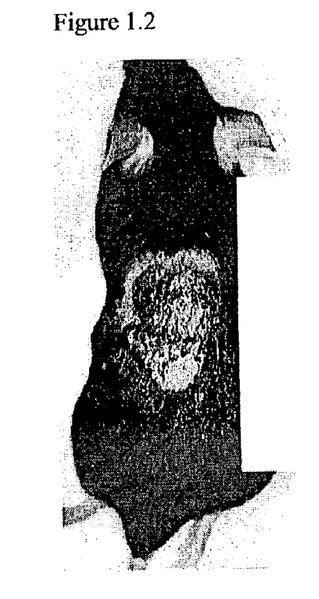
Figure 13:
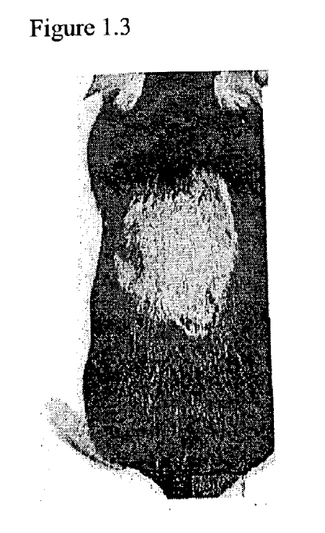
Figure 14:
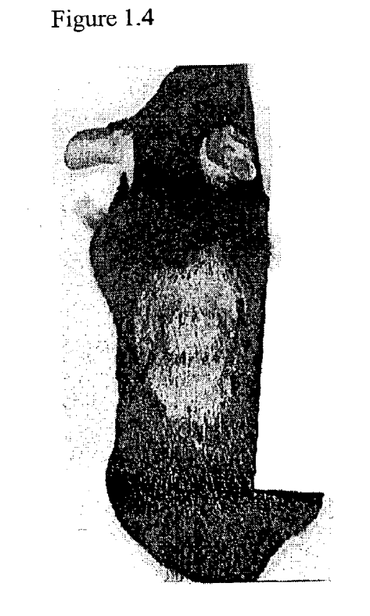
Figure 21:
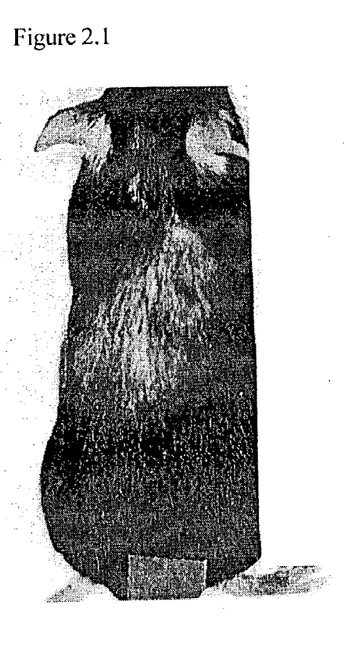
Figure 22:
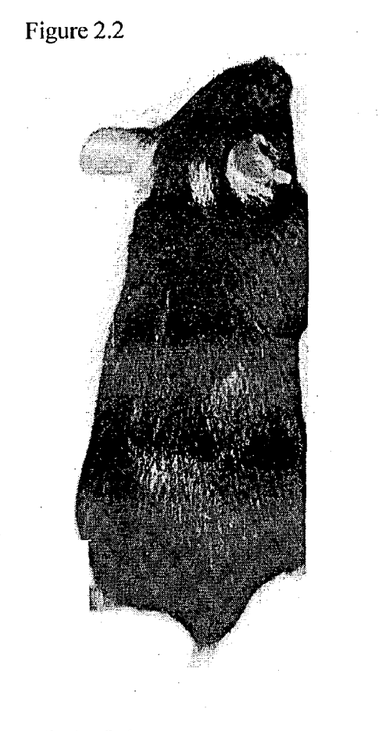
Figure 23:
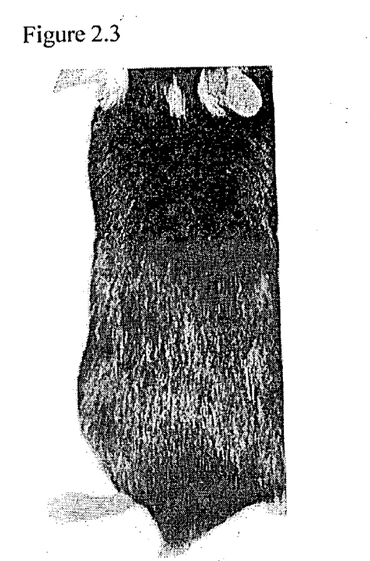
Figure 24:
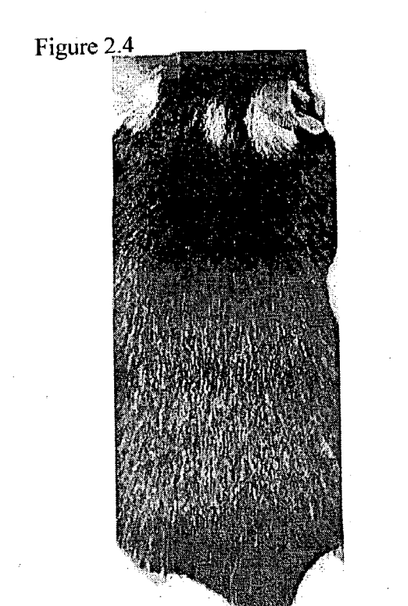

Photodynamic Therapy Treatment of C57BL/6 Mice with Alopecia of Unknown Etiology C57BL/6 mice used in this example were purchased from Jackson Laboratories (Bar Harbor, Me.). After 4 weeks of housing some of the C57BL/6 mice spontaneously developed a hair loss condition which resulted in large bald patches (see FIG. 1.1) at 12 to 14 weeks of age. One of these animals was sacrificed and skin samples were sent for histopathological evaluation. The skin sample showed no evidence of infection according to a veterinarian's histopathological examination. The condition was diagnosed as alopecia of unknown etiology. The presence of an undefined "mononuclear cell infiltrate" was noted within the affected skin and, without being bound by theory, may indicate an autoimmune etiology for alopecia in the mouse.

Eight mice that were developing hair loss were chosen. Four mice were randomly picked for the PDT treatment while the remaining four served as untreated controls. PDT consisted of intravenously injecting vertporfin in a lipid-based formulation (Visudyne®, Novartis Opthalmics, Duluth, Ga.) at a dosage of 1 mg/kg of body weight per mouse, followed by exposure to 690 nm wavelength red light at 15 J/cm², delivered by an array of light emitting diode (LED) panels, at 1 hour post-injection. (see Simkin G. et Al. 1997. Inhibition of contact hypersensitivity with different analogs of benzoporphyrin derivative. *Immunopharmacology* 37:221-230, which is incorporated by reference as if fully set forth). This was followed by two additional PDT treatments on days 7 and 14.

The mice were observed and photographed on days 0, 13, 21 and 28. FIGS. 1 and 2 show a representative untreated control and a PDT treated mouse photographed at day 0, day 13, day 21 and day 28. There was no improvement in the alopecic patches in the untreated control group of mice (n=4) and in fact, these patches worsened over the time course of the experiment (FIGS. 1.1 to 1.4). In the PDT treated group (n=4) there was a startling and impressive hair growth observed in the alopecic patches after the first and second treatments as demonstrated in FIGS. 2-2 and 2-3. By day 28, the previously alopecic patches were covered with what appeared to be a full complement of hair.

EXAMPLE 2

PDT-induced Stimulation of Hair Growth Using Topically-applied Photosensitizer

To prepare QLT 0074-containing ointment, QLT 0074 photosensitizer was dissolved in glacial acetic acid to solubilize it. The solution was then frozen in a dry ice/isopropanol bath and the acetic acid was removed by lyophilization. The resultant material was a fine fluffy powder. Analytical testing of the cryodessicated QLT 0074 indicated that the process did not cause degradation. The ointment base was prepared by first warming polyethylene glycol 200 (PEG 200) to 80-90° C. with stirring. Polyethylene glycol 3350 (PEG 3.35 K) was then added with stirring, followed by oleyl alcohol, and then diethylene glycol monoethyl ether. Stirring was continued until the solution was clear. The ointment base was cooled to approximately 50° C., and the QLT 0074 was added with stirring. Stirring was continued as the mixture cooled, until a homogenous paste was achieved. The ointment contained the following proportions of the components on a weight/weight basis.
QLT 0074 (1)
PEG-200 (108)
diethylene glycol monoethyl ether Transcutol® (40)
PEG-3.35K (32)
oleyl alcohol (20).

The concentration of QLT 0074 in the ointment was 0.5% weight/weight. A placebo ointment was prepared which contained the excipients, but lacked QLT 0074. The ointments were stored refrigerated at 2 to 8° C. until use.

Female Balb/C mice (8-14 weeks old) were supplied by Charles River Canada (St. Constance, Quebec). Mice were acclimated to laboratory conditions for seven days prior to release from quarantine. Cages of animals were held in enclosed ventilated animal racks in temperature and humidity controlled rooms. Mice were kept on a standard diet and water ad libitum in a 12 hours light/dark cycle. Mice were randomly assigned to PDT treatment and controlled groups, and were monitored for pain or distress.

Eighteen mice were shaved to remove hair from the back and both flanks. The right side of each mouse served as a control, receiving no light and no photosensitizer. QLT 0074-containing ointment was applied to a square spot on the left side of each of mice 1-9 using a square template, with the same quantity of ointment applied to each spot. Placebo formulation was applied to a square spot on the left side of each of mice 10-18 in the same manner. After 30 minutes, the excess ointment was removed from the spots by washing with water using a sterile gauze pad, and then placebo ointment was applied to the same spots on each of mice 1-18. After 15 minutes, the spots were irradiated with 50J/cm² of light delivered at a fluence rate of 200 mW/cm². Light (688 nm+/−6 nm) was delivered from a light emitting diode (LED) unit (Quantum, Model QB-Quanta-Med-688).

Figure 3:
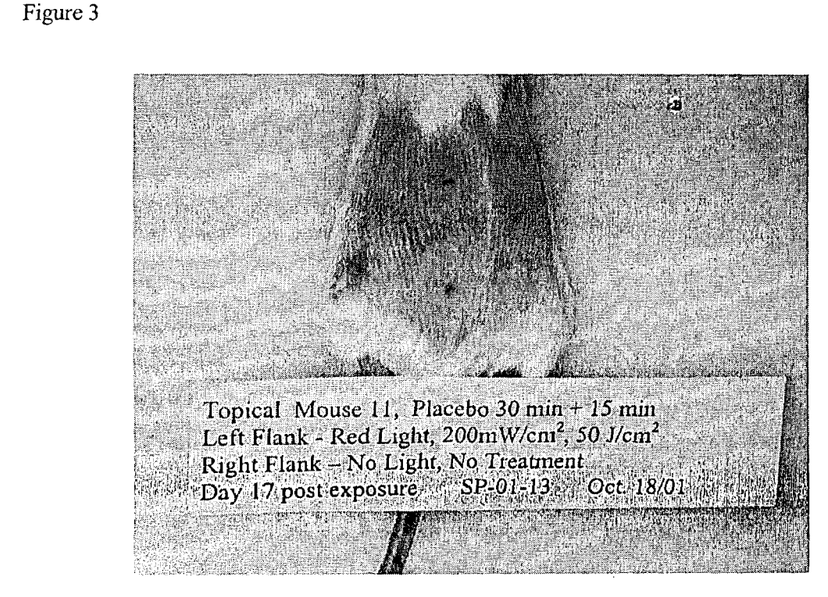
FIG. 3 is a photograph of a representative control Balb/c mouse that was shaved to remove hair, and subjected to a placebo PDT treatment (Example 2).
Figure 4:
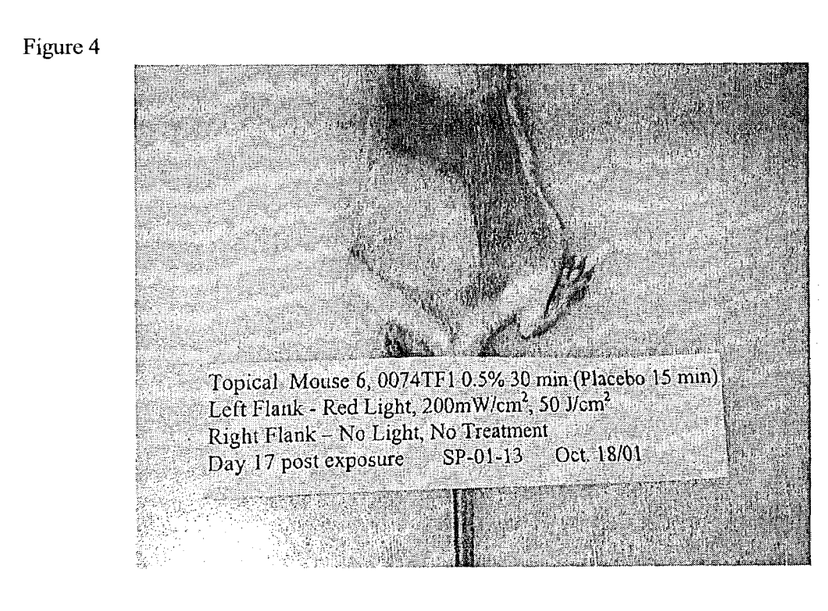
FIG. 4 is a photograph of a representative shaved Balb/c mouse that was shaved to remove hair, and subjected to a PDT treatment using the photosensitizer QLT 0074 (Example 2). Hair re-growth was observed 17 days after PDT treatment.

Out of the nine mice treated with QLT 0074, five developed hair growth on the treated area by day 17. In contrast, none of the placebo-treated mice developed hair regrowth on the area corresponding to the treatment area during that period. A photograph showing hair regrowth on the left side of a representative QLT 0074-treated mouse at day 17 is shown in FIG. 4. A mouse treated with placebo is shown in FIG. 3.

Similar results were obtained in another experiment in which mice were treated with the same formulation of 0.5% (w/w) QLT 0074, but a higher light dose of 150J/cm² was used.

EXAMPLE 3

Optimization of Irradiation Dose and Timing for Photodynamic Treatment of Alopecia Areata After Intravenous Injection of Photosensitizer This example examines the effect of different irradiation protocols on PDT treatment of alopecic mice as described above.

Alopecic mice are divided into control and treatment groups. The treatment mice are injected with verteporfin in a lipid-based formulation at 1 mg/kg of body weight, and the control group are mock injected. Mice from both groups are exposed to red light at the following doses: 1, 2, 5, 10 and 20 J/cm² light LED at 1 hour post-injection, in a manner as described above in Example 1. Two additional PDT treatments are administered on days 7 and 14 post photosensitizer administration. All mice are monitored over a 5 week period, photographed pre-treatment and on days 6, 13, 20, 27, and 34 post irradiation, and with biopsies taken for histopathological analysis.

In a separate experiment, alopecic mice are divided into control and treatment groups. The treatment mice are injected with verteporfin at 1 mg/kg of body weight, and the control group are mock injected. Mice from both groups are exposed to red light at 15 J/cm² light LED at 15, 30 and 60 120 and 180 minutes post-injection, in a manner as described above in Example 1. Two additional PDT treatments are administered on days 7 and 14 post photosensitizer administration. All mice are monitored over a 5 week period, photographed pre-treatment and on days 6, 13, 20, 27, and 34 post irradiation, and with biopsies taken for histopathological analysis.

EXAMPLE 4

Optimization of Drug Concentration, Irradiation Dose and Light Intensity on Hair Regrowth in Mice Using Topically-applied QLT-0074

A study was performed to assess the effect of drug concentration (0.005, 0.05, or 0.5% QLT 0074 ointment), light dose (50, 100 or 150 J/cm² red light) and light intensity 50 or 200 mW/cm) on hair regrowth in shaved female Balb/c mice. Mice received QLT 0074 ointment applied to the skin for 30 minutes, followed by a 15-minute treatment with placebo ointment and exposure to red light (688 nm). One group received no QLT 0074 ointment, only the placebo ointment and light exposure. Preparation of ointments and treatment procedure was as outlined in Example 2, except that different amounts of QLT 0074 were added.

Hair regrowth at the treatment site was observed in mice treated with a QLT 0074 ointment doses of 0.5% combined with light doses of 50, 100 or 150 J/cm$^2$ at 200 mW/cm$^2$. Hair regrowth at the treatment site was also observed for mice treated with 0.5% QLT 0074 ointment combined with either 50 or 100 J/cm$^2$ red light delivered at 50 mW/cm$^2$. Animals treated with 0.05% QLT 0074 ointment did not exhibit hair growth at any light dose, but hair regrowth at the treatment site was observed for one of three animals treated with 0.005% QLT 0074 ointment and 150 J/cm$^2$ delivered at 200 mW/cm$^2$. No hair regrowth occurred in mice that received placebo ointment only and were exposed to red light at 200mW/cm$^2$.

Ointments were prepared as in Example 2, except that different amounts of QLT 0074 (on a weight/weight basis) were incorporated into the ointments. The treatment procedure was as outlined in Example 2.

Mild skin reactions were evident following some treatments, typically at the highest drug and light dose combinations, but no moderate or severe skin photosensitivity reactions were observed.

EXAMPLE 5

Stimulation of Hair Growth in Human Subjects with AGA

A total of 10 subjects were treated. All subjects were human males over 18 years of age and had type II or III Vertex alopecia, rated according to the modified Hamilton-Norwood scale. All subjects received a single application of topical QLT0074 ointment 0.2% weight in weight (w/w) to two of three circular test sites on the vertex area of the scalp. The amount of ointment applied to each test site was approximately 224 mg (about 0.44 mg of photosensitizer per test site). After 2 hours the excess drug was removed and red light (LED's—690 nm) was administered to two of the three sites. The other test site served as a control with no drug or light administration.

Two light dose cohorts (50 and 75 J/cm$^2$) were investigated with each cohort having 5 subjects.

Safety was assessed by monitoring all adverse events during and after the treatment. No serious adverse events were reported.

The efficacy was assessed by hair counts 3 months after the treatment and compared to baseline counts. These results are shown in Table 3:

TABLE 3

|  | 50 J/cm$^2$ (% change in terminal hair count) | 75 J/cm$^2$ (% change in terminal hair count) |
| --- | --- | --- |
| Drug | +8% | +4% |
| Control |  | −1.7% |

These results show that a single PDT treatment can produce an increase in hair count in subjects having AGA associated hair loss.

EXAMPLE 6

Stimulation of Hair Growth in a Mouse Model of Alopecia Areata

A disease closely resembling human alopecia areata has been observed in aging (over 6-month old) C3H/HeJ mice (see Sundberg, J. P et al, Alopecia Areata in Aging C3H/HeJ Mice, Journal of Investigative Dermatology 102(6): 847-856 [1994[). The C3H/HeJ mouse model has become recognized as a good model for the study of the etiology and pathogenesis of alopecia areata and for the evaluation of treatments for the disease (McElwee, K. J. et al, Comparison of Alopecia areata in Human and Nonhuman Mammalian Species, Pathobiology 66:90-107 (1998). A study was carried out to determine if topical application of QLT0074 ointment could influence hair re-growth on C3H/HeJ female mice exhibiting hair loss. The C3H/HeJ mice were obtained from the Jackson Laboratories, Bar Harbor, Me. Three animals received QLT0074 ointment, prepared as outlined in Example 2, at 0.2% (w/w) applied onto balding areas of skin, 1.5×1.5 cm in area. All other areas outside of the treatment site were left untreated.

Following this treatment, all 3 mice received a dose of 50 J/cm$^2$ 688 nm light delivered at a rate of 50 mw/cm$^2$ in the 1.5 square area. Mice were monitored for skin photosensitivity reactions on Days 1 and 3 after light exposure and observed for hair re-growth for up to 19 days post-treatment. With QLT0074 ointment and red light treatment, no skin photosensitivity reactions were observed for mice treated with light. At day 7 post-treatment, an increased amount of hair was observed in the treatment area of 2 of the 3 mice treated.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

We claim:

1. A method of treating skin tissue on a subject's skin exhibiting, or suspected of, hair growth reduction or hair loss, which method comprises
    administering to said skin tissue an effective amount of photosensitizer capable of being activated by absorbing a wavelength of light of from about 400 to about 900 nm and capable of penetrating into the tissue to result in a desired degree of biodistribution; and
    irradiating said skin tissue with light containing a wavelength of about 400 to about 900 nm; and
    optionally repeating said administering and irradiating over time as needed to result in a desired level of hair growth in said skin tissue;
    wherein said effective amount of a photosensitizer is in the range of about 0.005 to about 10 mg/kg body weight of said subject.

2. The method of claim 1 wherein said photosensitizer is administered locally.

3. The method of claim 1 wherein said photosensitizer is administered intravenously, orally, subcutaneously, intramuscularly, intraperitoneally, intradermally, topically, or by use of an implant.

4. The method of claim 1 wherein the photosensitizer is administered in the form of a topical formulation having a viscosity at 20° C. of from about 50 cps to about 50000 cps.

5. The method of claim 1 wherein said irradiating is localized to the skin tissue exhibiting, or suspected of, hair growth reduction or hair loss.

6. The method of claim 1 wherein the photosensitizer is selected from a pro-porphyrin, a porphyrin, and mixtures thereof.

7. The method of claim 6 wherein said porphyrin is a BPD selected from BPD-MA, EA6, or B3.

8. The method according to claim 1 wherein said light totals a dose that does not exceed 200 J/cm$^2$.

9. The method according to claim 1 wherein said subject has been diagnosed as suffering from hair loss.

10. The method of claim 9 wherein said hair loss is due to androgenetic alopecia, alopecia areata, drug-induced alopecia, or radiation induced alopecia.

11. The method according to claim 1 wherein said subject has been diagnosed with androgenetic alopecia.

12. The method according to claim 1 further comprising treating said subject with at least one non-photodynamic treatment selected from 5-alpha reductase inhibitors, minoxidil, hair transplantation, scalp reduction, and combinations thereof.

13. The method of claim 1 comprising increasing the number of terminal hairs on the skin tissue.

14. A method of stimulating hair growth comprising increasing the number of terminal hairs on skin of a subject in need of such treatment by administering photosensitizer to an area of said skin, and irradiating the area with electromagnetic energy containing a wavelength appropriate to activate the photosensitizer,
wherein the photosensitizer is delivered in the amount of about 0.005 to about 10 mg/kg body weight of said subject.

15. The method according to claim 14 wherein the subject has been diagnosed as suffering from hair loss.

16. The method according to claim 14 further comprising selecting a subject diagnosed with androgenetic alopecia.

17. The method of claim 14 wherein there is 3% or more increase in the number of terminal hairs in the treated area within 3 months.

18. The method of claim 14 wherein the photosensitizer is administered topically to the area where hair growth is desired.

19. The method of claim 14 wherein the photosensitizer is administered in the form of a topical formulation having a viscosity at 20° C. of from about 50 cps to about 50000 cps.

20. The method according to claim 14 wherein said irradiating is localized to the treated area of skin.

21. The method of claim 14 wherein the photosensitizer is selected from a pro-porphyrin, a porphyrin, and mixtures thereof.

22. The method according to claim 14 wherein said energy is delivered 5 minutes to 4 hours after the administration of the photosensitizer.

23. The method according to claim 14 wherein said energy does not exceed 200 J/cm$^2$.

24. The method according to claim 14 further comprising treating the subject with at least one non-photodynamic treatment that causes an increase in the number of terminal hairs within the treatment area.

25. The method according to claim 24 wherein the subject is treated with at least one non-photodynamic treatment selected from 5-alpha reductase inhibitors, minoxidil, hair transplantation, scalp reduction, and combinations thereof.

26. The method of claim 14, wherein there is 2% or more increase in the number of terminal hairs in the treated area within three months.

27. A method of comprising increasing the number of terminal hairs on the skin of a subject in need of such treatment by administering a photosensitizer to an area of the skin; and
irradiating that area with electromagnetic energy of an appropriate wavelength to activate the photosensitizer and increase the level of one or more pro-inflammatory cytokines,
wherein the photosensitizer is delivered in the amount of about 0.005 to about 10 mg/kg body weight of said subject.

28. The method according to claim 27 wherein the one or more pro-inflammatory cytokines is selected from granulocyte-macrophage colony stimulating factor, interleukin-1-β, interleukin-1-α, and combinations thereof.

29. The method according to claim 27 further comprising selecting a subject suffering from hair loss caused by androgenetic alopecia.

30. The method of claim 27, wherein there is 2% or more increase in the number of terminal hairs in the treated area within three months.

31. A method of comprising increasing the number of terminal hairs on skin of a subject in need of such treatment by administering photosensitizer to an area of the skin, and irradiating the area with electromagnetic energy containing a wavelength appropriate to activate the photosensitizer,
wherein the treatment delivers a low dose of PDT,
wherein the photosensitizer is delivered in the amount of about 0.005 to about 10 mg/kg body weight of said subject.

32. The method according to claim 31 wherein said increasing step results in a 2% or more increase in the number of terminal hairs in said area within 3 months.

33. The method according to claim 31 further comprising selecting a subject suffering from hair loss caused by androgenetic alopecia.

34. The method according to claim 31 wherein the photosensitizer is administered in the form of a topical formulation having a viscosity at 20° C. of from about 50 cps to about 50000 cps.

35. The method according to claim 31 wherein the photosensitizer is selected from a pro-porphyrin, a porphyrin, and mixtures thereof.

36. The method according to claim 31 wherein said energy does not exceed 200 J/cm$^2$.

37. A method of stimulating hair growth comprising administering photosensitizer to an area of skin of a subject where hair growth is desired;
irradiating the area with energy containing a wavelength appropriate to activate the photosensitizer; and optionally repeating said administering and irradiating steps,
wherein the photosensitizer is delivered in an amount of 0.005 to about 10 mg/kg body weight of said subject.

38. The method of claim 37 wherein said photosensitizer is administered locally.

39. The method of claim 37 wherein said photosensitizer is administered intravenously, orally, subcutaneously, intramuscularly, intraperitoneally, intradermally, topically, or by use of an implant.

40. The method of claim 37 wherein the photosensitizer is administered in the form of a topical formulation having a viscosity at 200° C. of from about 50 cps to about 50000 cps.

41. The method of claim 37 wherein said irradiating is localized to the skin tissue exhibiting, or suspected of, hair growth reduction or hair loss.

42. The method of claim 37 wherein the photosensitizer is selected from a pro-porphyrin, a porphyrin, and mixtures thereof.

43. The method according to claim 37 wherein said energy totals a dose that does not exceed 200 J/cm$^2$.

44. The method according to claim 37 wherein said subject has been diagnosed as suffering from hair loss.

45. The method according to claim 37 wherein said subject has been diagnosed with androgenetic alopecia.

46. The method according to claim 37 further comprising treating said subject with at least one non-photodynamic treatment selected from 5-alpha reductase inhibitors, minoxidil, hair transplantation, scalp reduction, and combinations thereof.

47. The method of claim 37 comprising increasing the number of terminal hairs on the skin tissue.

* * * * *